(12) United States Patent
Essenpreis

(10) Patent No.: US 6,659,966 B2
(45) Date of Patent: Dec. 9, 2003

(54) FLUID SAMPLING APPARATUS

(75) Inventor: Matthias Essenpreis, Fremont, CA (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 10/002,325

(22) Filed: Nov. 15, 2001

(65) Prior Publication Data

US 2003/0093010 A1 May 15, 2003

(51) Int. Cl.[7] .............................. A61B 5/00; B65D 81/00
(52) U.S. Cl. ...................... 600/583; 600/573; 606/181; 606/10
(58) Field of Search ................................. 600/573, 576, 600/579, 583, 584; 606/1, 3, 8, 10–13, 181–183, 185

(56) References Cited

U.S. PATENT DOCUMENTS

| | | | |
|---|---|---|---|
| 4,273,127 A | 6/1981 | Auth et al. ................... 606/3 |
| 4,816,224 A | 3/1989 | Vogel et al. .................. 422/55 |
| 4,924,879 A | 5/1990 | O'Brein ..................... 600/583 |
| 5,140,984 A * | 8/1992 | Dew et al. .................... 607/89 |
| 5,271,895 A | 12/1993 | McCroskey et al. .......... 422/58 |
| 5,304,170 A | 4/1994 | Green .......................... 606/9 |
| 5,382,523 A | 1/1995 | Hoenes et al. ............... 435/14 |
| 5,554,153 A | 9/1996 | Costello et al. ................ 606/9 |
| 5,695,493 A | 12/1997 | Nakajima et al. ............. 606/13 |
| 5,702,360 A | 12/1997 | Dieras et al. .................. 604/22 |
| RE35,803 E | 5/1998 | Lange et al. ................. 606/182 |
| 5,839,446 A | 11/1998 | Waner et al. ................ 128/898 |
| 5,846,837 A | 12/1998 | Thym et al. ................. 436/170 |
| 5,908,416 A | 6/1999 | Costello et al. ................ 606/9 |
| 5,947,957 A | 9/1999 | Morris ......................... 606/13 |
| 5,997,817 A | 12/1999 | Crismore et al. ............. 422/58 |
| 6,074,383 A | 6/2000 | Grippi et al. .................. 606/14 |
| 6,152,919 A | 11/2000 | Hakky ......................... 606/15 |
| 6,155,992 A | 12/2000 | Henning et al. ............. 600/583 |
| 6,183,489 B1 | 2/2001 | Douglas et al. ............. 606/181 |
| 6,261,245 B1 * | 7/2001 | Kawai et al. ................ 600/576 |
| 6,352,514 B1 * | 3/2002 | Douglas et al. ............. 600/583 |
| 6,423,011 B1 * | 7/2002 | Arulkumaran et al. ....... 600/576 |
| 6,503,209 B2 * | 1/2003 | Hakky et al. ................ 600/573 |

OTHER PUBLICATIONS

M.J.C. van Gemert et al., "Laser Treatment of Port Wine Stains", Optical–Thermal Reponse of Laser–Irradiated Tissue, edited by A.J. Welch and M.J.C. van Germert, Plenum Press, New York, 1995 (pp789–829).

* cited by examiner

*Primary Examiner*—Charles Marmor
(74) *Attorney, Agent, or Firm*—Jill L. Woodburn

(57) ABSTRACT

A fluid sampling apparatus is provided that in accordance with the present invention. The apparatus includes a housing defining a chamber, a lancet positioned in the chamber and including an end formed to create a fluid collection incision, and a light source positioned in the chamber. The light source is formed to emit a light beam of a pre-determined wavelength and for a time sufficient to seal the incision.

21 Claims, 5 Drawing Sheets

FLUID SAMPLING APPARATUS

FIELD OF THE INVENTION

The present invention is directed to an apparatus and method of obtaining a sample of fluid from a user for subsequent diagnostic tests.

BACKGROUND AND SUMMARY OF THE INVENTION

Capillary blood sampling is a process for obtaining blood samples from the subdermal capillary beds of users. A common method is to produce a small incision in the user's skin using a sharp needle or small blade, called a blood lancet. See, for example, U.S. Pat. Nos. 6,183,489, 5,554,166, 4,924,879, and Re. 35,803, the disclosures of which are hereby incorporated herein by reference. These existing blood lancets are mostly mechanical devices that use steel lancets to penetrate the skin and damage blood vessels to obtain a blood sample. It is also known to use lasers for perforating materials such as skin tissue. See, for example U.S. Pat. Nos. 6,074,383, 5,947,957, 5,908,416, 5,839,446, and 5,554,153. These existing laser lancets replace the mechanical lancing mechanism through laser perforation of the skin.

Coagulation of bleeding wounds has been used in laser-assisted surgery, such as burn wound removal and surgery on highly-vascularized organs such as the liver for many years. See for example, U.S. Pat. No. 4,273,127, which discloses a cutting and coagulating device for use for relatively bloodless surgery. The laser light penetrates the tissue to deeply coagulate the tissue and produce a clot of sufficient size to allow adequate coagulation, stopping the bleeding.

In addition, lasers have been used to treat congenital vascular malformations, such as port wine stains. See for example, M. J. C. van Gemert et al., "Laser Treatment of Port Wine Stains", Optical-Thermal Response of Laser-Irradiated Tissue, edited by A. J. Welch and M. J. C. van Gemert, Plenum Press, New York, 1995 (pp789–829). In such a treatment, the laser illumination leads to coagulation of the red blood cells and, by heat conduction, to transmural coagulation of the vessel wall of the ectatic vessel. Ideal wound healing occurs several months later when the ectatic vessels are replaced by one or more "normal" capillaries.

The present invention provides a method and apparatus for obtaining a sample of fluid from a user for diagnostic testing and for sealing the incision following the sampling. The apparatus comprises a housing defining a chamber, a lancet positioned in the chamber and including an end formed to create a fluid collection incision, and a light source positioned in the chamber, the light source formed to emit a light beam of a pre-determined wavelength and for a time sufficient to seal the incision.

According to another aspect of the invention a fluid sampling apparatus is provided. The apparatus comprises a housing defining a chamber, a lancet positioned in the chamber and including an end formed to create a fluid collection incision, means for collecting blood from the open incision, and a light source coupled to the housing, the light source emitting light of a pre-determined wavelength and for a time sufficient to seal the incision following withdrawal of the blood.

According to still another aspect of the invention a method is provided for controlling a fluid collection incision. The method comprises the steps of lancing a portion of skin of a user to create a fluid collection incision, and exposing the fluid collection incision to light having a pre-determined wavelength and for a time sufficient to seal the incision following withdrawal of the blood.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

The present invention provides a method and apparatus for obtaining a sample of fluid from a user and for effectively and minimally invasively closing the incision that remains after sampling of small fluid volumes through the skin of a user. Such a method and apparatus is particularly useful for blood glucose monitoring. The apparatus of the present invention forms a very small spot at a fluid collection incision, which is the origin of the fluid flow. After the fluid sample is collected, the fluid collection incision is irradiated with a light source, closing the spot without damage to the surrounding tissue. Aspects of the invention are presented in FIGS. 1–4, which are not drawn to scale and wherein like components in the several views are numbered alike.

A sampling apparatus 10 is provided in accordance with the invention that includes a housing 12. A lancet mechanism 14 and a light source 16, preferably a laser diode, are disposed in the housing 12. The sampling apparatus 10 is formed with disposable lancet components. It is appreciated that the sampling apparatus 10, however, may be formed with any number of disposable components in accordance with this disclosure.

Figure 1:
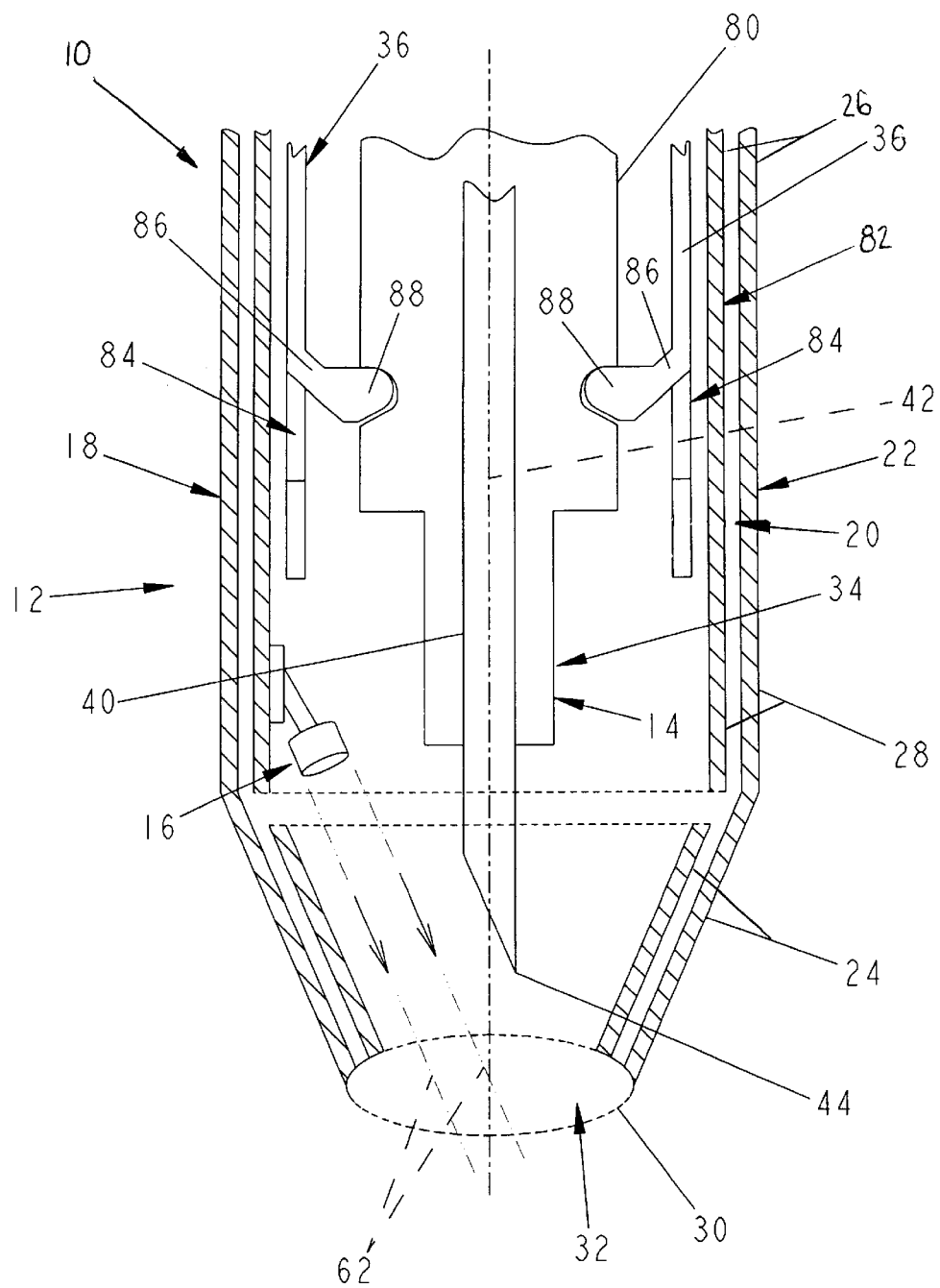
FIG. 1 is a representation of a sampling apparatus of the present invention.

Referring now to FIG. 1, the housing 12 includes a body 18, which defines a chamber 20 therein. The body 18 includes a cylindrical sleeve 22 having a tapered proximal end 24, an opposed distal end 26, and a side wall 28. The proximal end 24 has a lower rim 30 that defines an opening 32 into chamber 20. The housing 12 can be of any shape, which may be readily adapted for use with the lancet mechanism 14 and the light source 16. Housing 12 is preferably constructed of a molded plastic material, although it is understood that a wide variety of materials and molding techniques may be used. In addition, it is preferred that at least the portion of the housing 12 adjacent to the light source 16 is substantially transparent. This transparency assists the user in aligning the device with the fluid-collection incision.

The disposable lancet mechanism 14 is situated adjacent to the proximal end 24 of the sleeve 22. The lancet mechanism 14 has an outer diameter that is smaller than the internal diameter of the sleeve 22. The internal wall of sleeve 22 thus forms a lancet guide during the puncturing and retraction movement of the lancet mechanism 14. As shown in FIG. 1, the lancet mechanism 14 includes a lancet 34 that is sized to fit into and move up and down in the chamber 20 formed in the housing 12. The lancet 34 sits in a lancet holder 36 in the chamber 20.

The lancet holder 36 itself includes a lancet take-up part 82 with two notches 84 from which tongues 86 extend. The tongues 86 each include a free end that is formed into a lug 88. The distance between said lugs 88 in a non-tensioned state is smaller than the internal diameter of the lancet holder 36. If a lancet 34 is positioned in the lancet holder 36, the tongues 86 form on the lancet 34 like a pair of tongs.

As shown in FIG. 1, the lancet 34 includes a plastic lancet body 80 and a metal lancet needle 40. The lancet needle 40 extends along a longitudinal axis 42, which is represented as a dashed line. The anterior end of the lancet needle 40 in the puncturing movement direction is formed as a sharp point 44. It is appreciated that the size of the lancet needle 40 can vary depending upon the amount of blood sample required. Needles with a larger length and width are used to create a larger incision when a greater blood sample is required. The puncturing and retraction movement of the lancet 34 is achieved by converting rotary movement about an axis of rotation of a spirally wound coiled spring (not shown) and of a transmission member (not shown) into longitudinal displacement of the lancet holder 36 in the direction of the predetermined puncturing movement direction along axis 42 and thereafter in the opposite direction.

It is appreciated that any number of different mechanical lancets can be located in the chamber 20 of the housing 12 in accordance with this disclosure. It is further appreciated that the size and shape of the housing can be altered to accommodate these lancets. All of the components of mechanical lancets are commercially available, and proper selection thereof would not require undue experimentation by one of ordinary skill in the art. Additional details concerning operation of the lancet 34, however, can be found in U.S. Pat. Nos. 4,924,879 and Re. 35,803, the disclosures of which is hereby incorporated herein by reference.

As shown in FIG. 1, the light source 16 is mounted in the chamber 20 of the housing 12. The light source 16 is coupled to the side wall 28 adjacent to the proximal end 24. It is appreciated that the light source 16 can be positioned in a variety of locations in the chamber 20. It is also appreciated that the light source 16 may be coupled to the housing 12 outside of the chamber 20 or removable from the housing 12 in accordance with this disclosure.

The light source 16 is formed to emit a light beam of a pre-determined wavelength and for a time sufficient to seal the fluid collection incision formed by the lancet mechanism 14 that remains after sampling of small fluid volumes from said incision. It is appreciated that an appropriate wavelength for sealing the fluid collection incision ranges from about 400 nm to about 1400 nm. Particularly, when the target fluid is blood, the appropriate wavelength can range from about 415 nm to about 600 nm, and more particularly when the target fluid is blood the appropriate wavelength is about 500 nm. At this wavelength, all other tissue constituents for example proteins, water, etc. have a much lower optical absorption of at least one order of magnitude.

Figure 2:
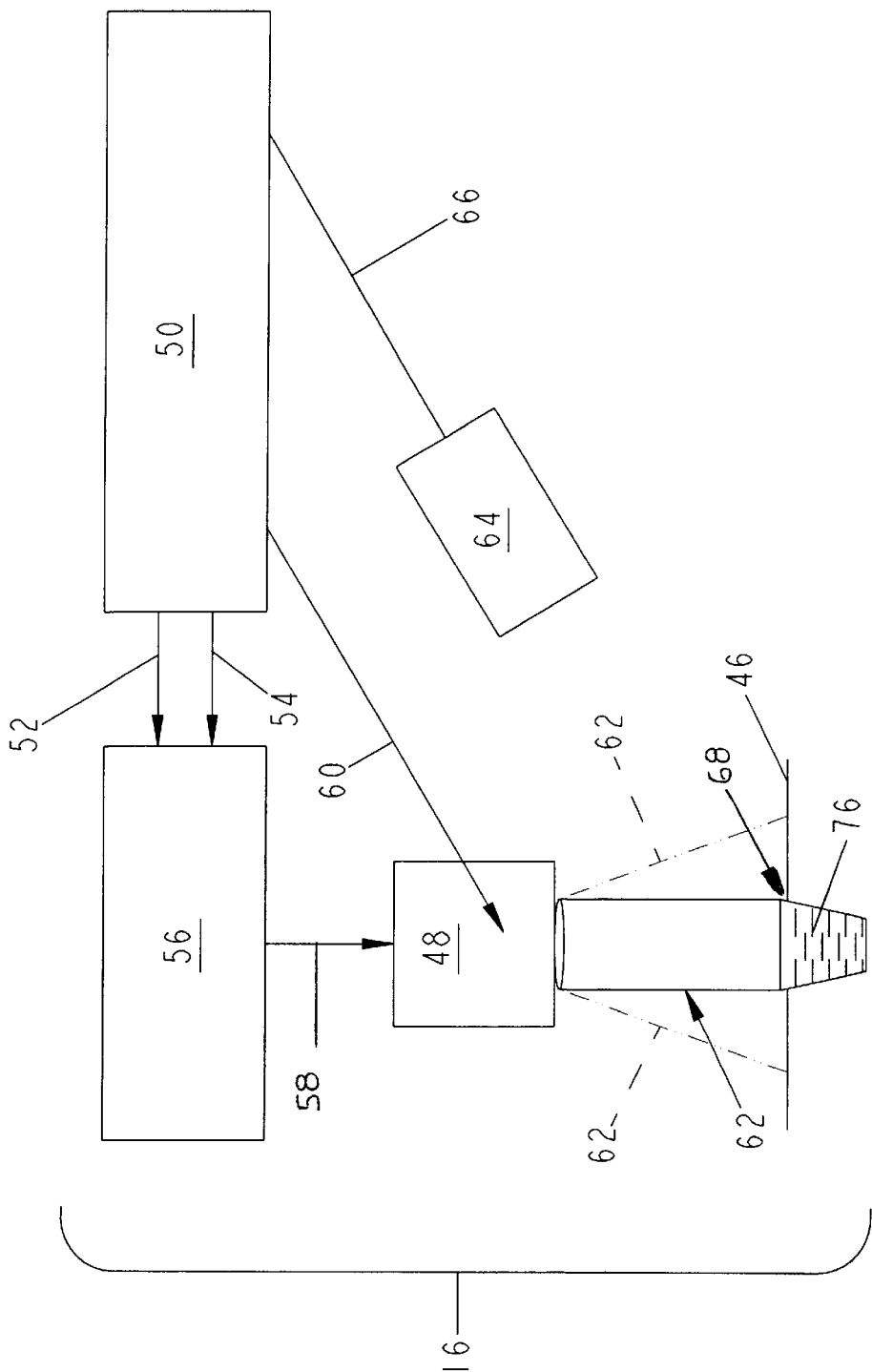
FIG. 2 is a diagrammatic view of a feedback mechanism of the laser device of the present invention.

Thus, when the light source 16 emits the appropriate wavelength, the absorbed energy of the light is beneficially directed into the fluid collection incision or blood vessel. The light energy is predominately absorbed by the fluid and since heat diffusion cannot take place sufficiently quickly, thermally coagulates the blood, generating a blood clot in and around the blood vessel(s). As the energy is delivered predominately to the hemoglobin and the parameters are selected such that heat diffusion is slower than energy delivery, the blood is thermally coagulated, resulting in a seal of the bleeding vessel. It is appreciated that the appropriate wavelength necessary to seal the collection incision may vary depending upon the accuracy of delivery of the light as well as the volume of blood present. As will be discussed hereafter, feedback control can also be used to estimate the size of blood volume to be coagulated and therefore enable the user to minimize the wavelength of the administered light. As shown in FIG. 2, the light source 16 is preferably a laser diode 48. It is preferred that the laser diode 48 be a low-cost solid state laser capable of delivering energy at the surface of the skin targeted at about 400 to 1400 nm. The energy delivered by the laser diode 48 depends upon the accuracy of delivery as well as the fluid volume at the incision. The laser diode 48 is capable of delivering energy at the surface of skin targeted for a variety of time periods. Non-limiting examples of suitable periods include from about 0.1 second to about 1 second, more particularly about 0.56 seconds. Further, it is appreciated in accordance with at least one aspect of the present invention, that the laser diode 48 be sufficiently small to be portable and inserted into the chamber 20 of the sampling apparatus 10. Laser diodes 48 suitable for the present invention are conventional and are commercially available. A non-limiting example of such a laser includes, but is not limited to, the GLP-05-B, 5 mW, 532 nm laser commercially available from Changchun New Industries Optoelectronics Tech. Co., Ltd. Changchun, P.R. China. A preferred laser device is a collimated laser diode. It is appreciated that other light sources, non-limiting examples of which include LED's may be used in accordance with this disclosure in place of the laser diode.

The light source 16 used in accordance with the present invention includes a lens assembly 78 (FIG. 4) for collimating and focusing light from the light source 16 onto the surface of a user's skin 46 (FIG. 2). The lens assembly 78 can be integrated with the laser diode 48 and includes at least one lens. The number and arrangement of individual lenses for collimating and focusing is well-known to one of ordinary skill in the art. It is appreciated that the lens assembly can be either integrated with or distinct from the laser diode 48 in accordance with this disclosure. It is further appreciated that the light source 16 of the present invention may be formed without a lens assembly in accordance with the present disclosure.

Referring again to FIG. 2, the light source 16 further includes a controller 50 and a power supply 56. The controller 50 generates the master timing and controls all programmed operations of the laser diode 48. In particular, the controller 50 generates signals that correspond to power settings and pulse durations, as shown by arrows 52 and 54 respectively. These signals 52, 54 are each sent to the power supply 56. The power supply 56, in turn forwards the appropriate power and pulse to the laser diode 48, as shown by arrow 58. It is preferred that the controller 50 is a pulse generator that generates pulses as the form of signal. Alternatively, the controller 50 can be a function generator. Although the controller 50 is shown diagrammatically as a single component, it is appreciated that the controller may be constructed of distinct components.

The depth of irradiation by the laser light beam 62 into a fluid collection incision 68 is controlled by variable parameters, which include laser power, pulse duration, focal length, and position of the laser diode 48 relative to the skin 46. The laser pulse duration and the magnitude of the pulse are selected by the controller 50 to achieve efficient rates of tissue closure.

It is appreciated that the thermal relaxation time of the skin 46 depends on the size of the opening of the fluid collection incision 68 as well volume of blood 76 present in the incision 68. Feedback control can also be used to determine the thermal relaxation time by estimating the size of blood volume to be coagulated in accordance with this disclosure. This feedback control is preferably accomplished by cooperation between the controller 50 and an optical detector 64. See FIG. 2. The optical detector is preferably a photodiode, which detects the size of the bleeding spot on the skin 46 of the user. It is appreciated that any number of commercially available photodiodes can be used in accordance with the present disclosure. Alternatively, it is appreciated that a variety of imaging devices such as charged coupled device (CCD) arrays, video cameras, etc. used alone or in combination with any number of imaging algorithms can also be used in accordance with the present disclosure.

The optical information gathered by detector 64 is provided as shown by arrow 66 to the controller 50. Controller 50 in turn sends a signal related to a focal length position, as shown by arrow 60, to the laser 48 as well as power setting and duration signals 52, 54 respectively to the power supply 56. The feedback control can also be used to control the laser location and extension of the illuminated site by "focusing" the laser light (with a similar mechanism as in today's auto-focus cameras).

It is appreciated that each of the foregoing functions performed by components of the light source 16 (e.g. controller 50, power supply 56, and optical detector 64) can be carried out by a separate component, or, in the alternative, two or more of the foregoing functions may be carried out by an individual component formed to perform said functions in accordance with this disclosure. All of the components described herein are commercially available, and proper selection thereof would not require undue experimentation by one of ordinary skill in the art.

Sampling apparatus 10 forms the fluid collection incision 68, which is the origin of the fluid flow. The fluid, preferably blood, can be removed from the skin 46 using a variety of well known commercially available test strips. Non-limiting examples of suitable strips include U.S. Pat. Nos. 5,997,817, 5,846,837, 5,382,523, 5,271,895, 4,816,224, the disclosures of which are hereby incorporated herein by reference. It is appreciated, however, that any number of containers, applicators, biosensors, etc. may be used to collect the fluid from the skin 46 of the user for analytical testing for a variety of analytes. Non-limiting examples of such analytes includes, glucose, cholesterol, triglycerides, lactate, pyruvate, alcohol, bilirubin, uric acids, and drugs.

Figure 3A:
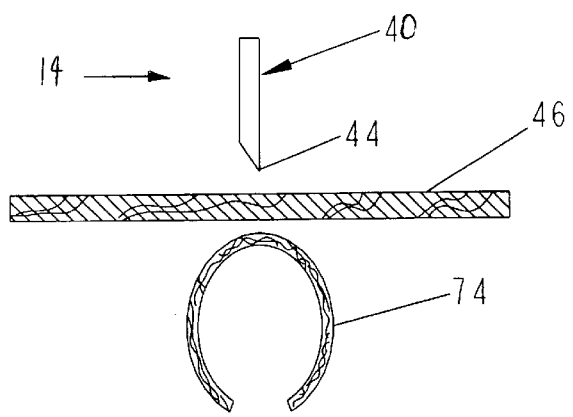
FIGS. 3A–3F are views illustrating an aspect of the method of the present invention.
Figure 3B:
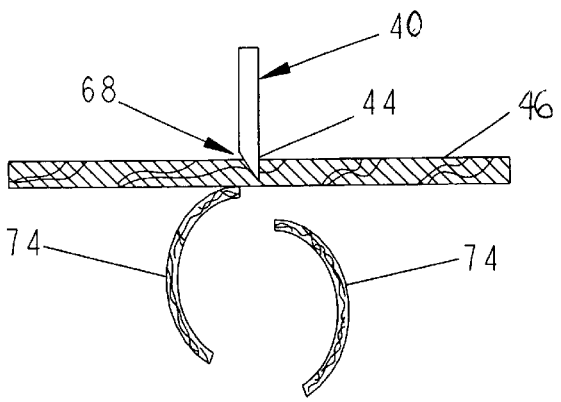
Figure 3C:
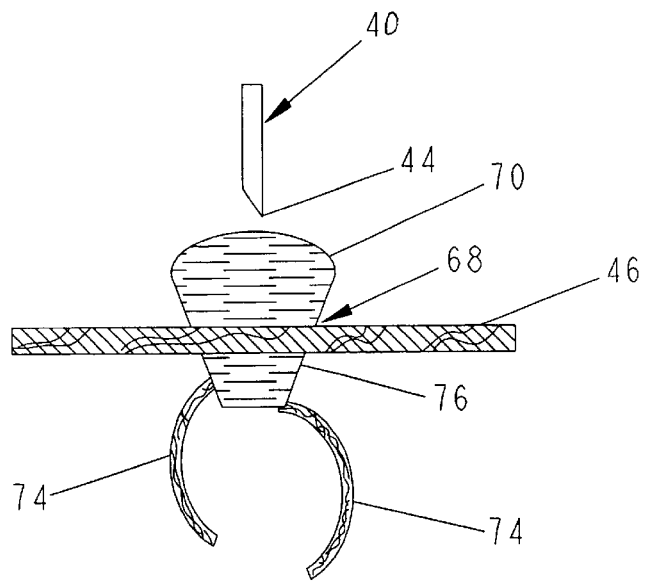
Figure 3D:
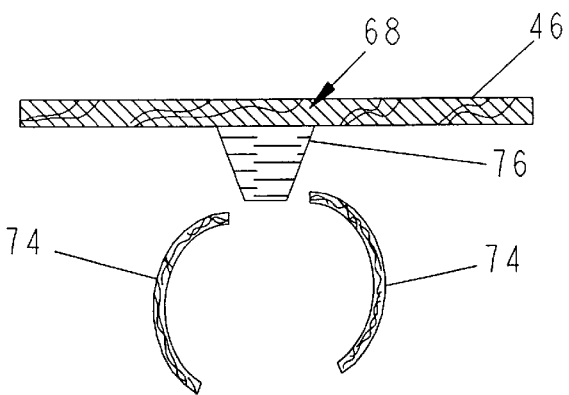

Use of the sampling apparatus 10 is illustrated in FIGS. 3A–3F. As shown in FIGS. 3A–3B, the lancet needle 40 of the lancet mechanism 14 is aligned with a body part, such as the skin 46 of a user. Preferably, the fluid collection incision 68 is formed on either the arm or the fingertip of the user. Although it is appreciated that the user is free to select any one of a variety of body parts in accordance with this disclosure. The lancet mechanism 14 is activated so that the sharp point 44 of the lancet needle 40 forms a small puncture spot through skin of a user, creating the fluid collection incision 68. This fluid collection incision 68 may be formed on any body part of a user. The diameter of the incision 68 can vary. Non-limiting examples range from about 0.4 mm to about 2 mm, more particularly about 0.4 mm to about 0.9 mm in diameter.

Upon forming the incision 68, the lancet needle 40 lances blood vessel(s) 74 of the user, (FIG. 3B) triggering bleeding.

Figure 3E:
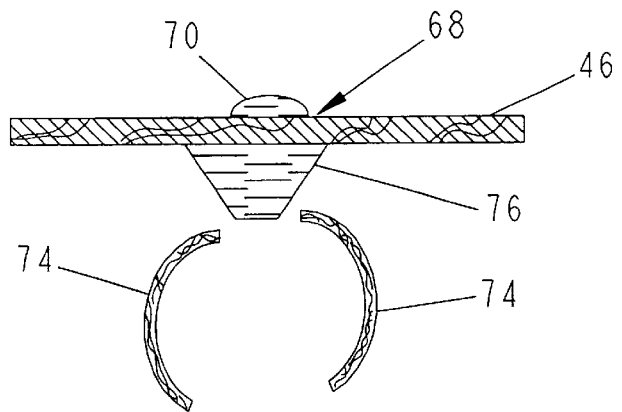
Figure 3F:
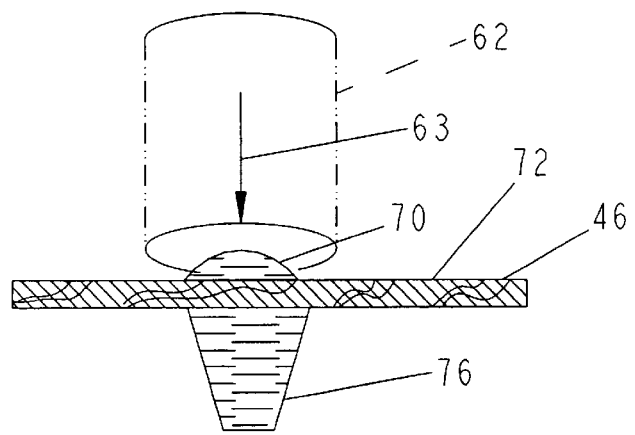

The bleeding of the lanced blood vessel(s) 74 forms a pool of blood 76 under the skin 46, which flows through the skin 46 at the fluid collection incision 68 and creates exposed blood 70. See FIG. 3C. After the blood 70 is removed from the skin by sampling into a determination entity such as a test strip (not shown) for sampling (FIG. 3D), additional blood 70 may continue to bleed from the incision 68 (FIG. 3E). The incision 68 is then irradiated with light 62 (FIG. 3F) in the direction of arrow 63 where the light wavelength and pulse duration are selected such that sealing of the incision is assured whilst minimizing the damaging effect on the surrounding tissue 72.

Figure 4:
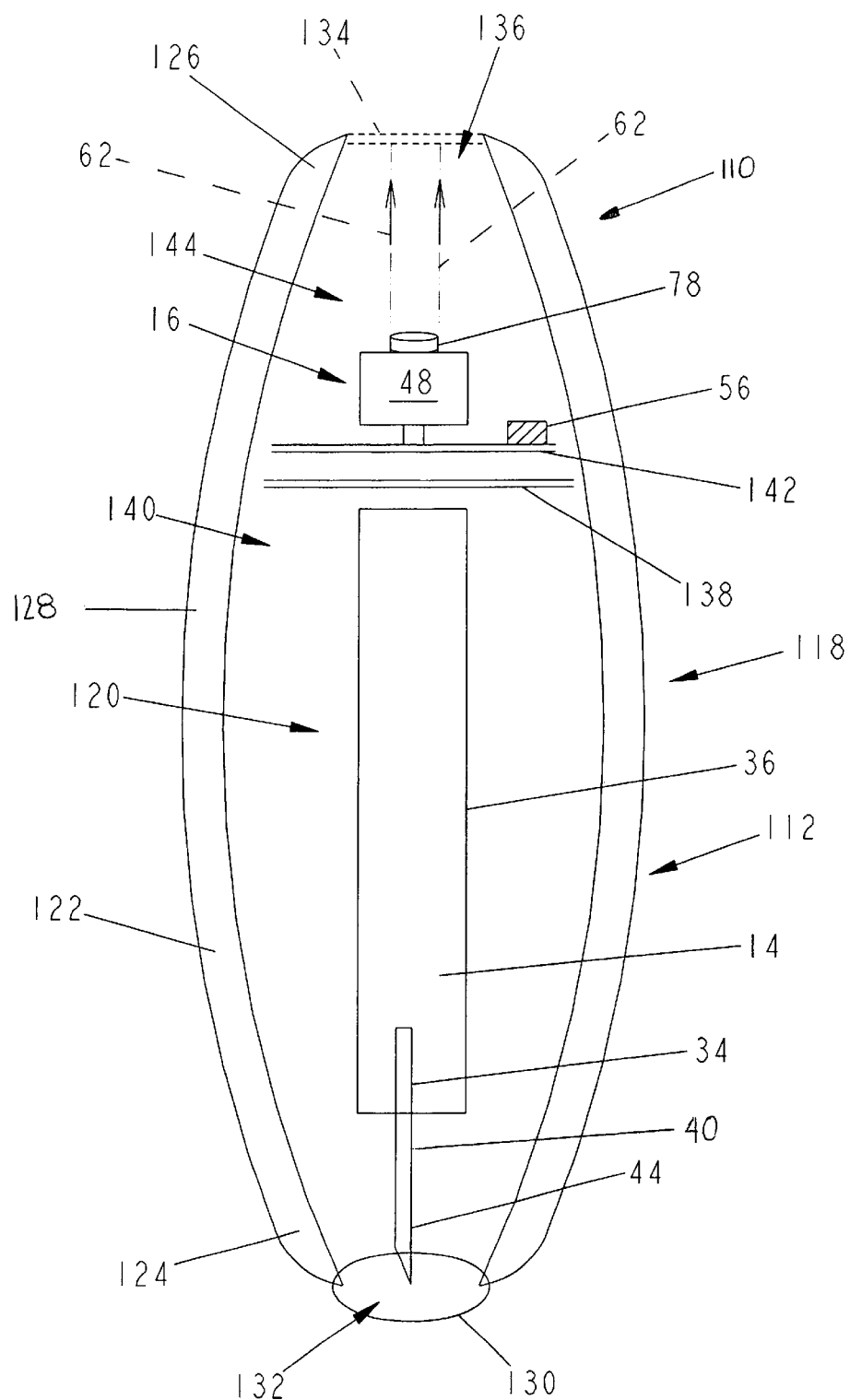
FIG. 4 is a representation of a sampling apparatus of another aspect of the present invention.

In accordance with another aspect of the present invention, a sampling apparatus 110 is provided. Apparatus 110 is shown in FIG. 4 and includes the lancet mechanism 14 and the light source 16 disposed within a chamber 120 of a housing 112. While not illustrated in FIG. 4, it is appreciated that the lancet mechanism 14 is coupled to the housing 112 in the manner described above with reference to the sampling apparatus 10. In addition, it is appreciated that the puncturing and retraction movement of the lancet 34 is achieved as discussed above with reference to the sampling apparatus 10. Additional details concerning operation of the lancet 34, however, can be found in U.S. Pat. Nos. 4,924,879 and Re. 35,803, the disclosures of which is hereby incorporated herein by reference.

The housing 112 of the sampling apparatus 110 includes a body 118, which defines the chamber 120 therein. The body 118 includes a sleeve 122 having a tapered proximal end 124, an opposed tapered distal end 126, and a side wall 128. While the housing 112 is shaped for use with the lancet mechanism 14 and the light source 16 illustrated in FIGS. 1–3, it is appreciated that it may have any number of shapes and sizes to accommodate a variety of commercially available lancets in accordance with this disclosure. It is also appreciated that housing 112 is constructed of similar materials and is preferably substantially transparent adjacent to at least the distal end 126. Although body 118 is illustrated as including a one-piece sleeve, it is appreciated that proximal and distal ends 124, 126 can be formed as separate components. Such a design enables the user of apparatus 110 to discard the lancet mechanism 14 following use and to reuse the light source 16 with a new lancet mechanism.

As shown in FIG. 4, the proximal end 124 of the sleeve 122 has a lower rim 130 that defines an opening 132 into the chamber 120. The distal end 126 also is formed with an upper rim 134 that defines an opening 136 into the chamber 120. In addition, the housing 112 includes a first plate 138 that extends across the chamber 120 and cooperates with the proximal end 124 to define a first section 140 containing the lancet mechanism 14. The housing 112 also includes a second plate 142 that extends across the chamber 120 and cooperates with the distal end 126 to define a second section 144 containing the light source 16. This second plate 142 is preferably an electronic circuit board for the light source 16.

In use, the proximal end 124 of the sampling apparatus 110 is aligned with a body part, such as the skin 46 of a user where said user desires to form a fluid collection incision 68. Preferably, the fluid collection incision 68 is formed on either the arm or the fingertip of the user. Although it is appreciated that the user is free to select any one of a variety of body parts in accordance with this disclosure. The lancet mechanism 14 is activated so that the sharp point 44 of the lancet needle 40 forms a small puncture spot through skin of a user, creating the fluid collection incision.

Fluid, such as blood 70 is collected from the collection incision 68 as described above with reference to FIG. 3.

After the fluid is collected, the user aligns the distal end 126 of the sampling apparatus 110 with the fluid collection incision 68. The end 126 is placed against the skin 46 and the incision is then irradiated with light where the light wavelength and pulse duration are selected such that the incision is sealed.

Although the invention has been described in detail with reference to a preferred embodiment, variations and modifications exist within the scope and spirit of the invention, on as described and defined in the following claims.

What is claimed is:

1. A fluid sampling apparatus comprising:
   a housing defining a chamber having an opening,
   a lancet positioned in the chamber and including an end formed to create a fluid collection incision, and
   a light source positioned in the chamber, the light source fanned to emit a light beam through the opening of the housing into the fluid collection incision, the light beam being of a pre-determined wavelength and for a time sufficient to seal the incision.

2. The apparatus of claim 1 wherein the pre-determined wavelength ranges from about 400 nm to about 1400 nm.

3. The apparatus of claim 2 wherein the pre-determined wavelength ranges from about 415 nm to about 600 mm.

4. The apparatus of claim 1 wherein the light source is a laser diode.

5. The apparatus of claim 1 wherein the time ranges from about 0.1 second to about 1 second.

6. The apparatus of claim 5 wherein the time is about 0.56 seconds.

7. The apparatus of claim 1 further comprising a feedback control that is formed to determine a thermal relaxation time of the incision.

8. The apparatus of claim 7 wherein the feedback control includes a controller in communication with the light source and an optical detector in communication with the controller.

9. The apparatus of claim 8 wherein the optical detector is a photodiode.

10. The apparatus of claim 1 wherein at least a portion of the housing is transparent.

11. A fluid sampling apparatus, the apparatus comprising:
    a housing defining a chamber having an opening,
    a lancet positioned in the chamber and including an end formed to create a fluid collection incision.
    means for collecting blood from the open incision, and
    a light source coupled to the housing, the light source emitting light through the opening of the housing into the incision, the light being of a pre-determined wavelength and for a time sufficient to seal the incision following withdrawal of the blood.

12. The apparatus of claim 11 wherein the pre-determined wavelength ranges from about 400 nm to about 1400 nm.

13. The apparatus of claim 11 wherein the time ranges from about 0.1 second to about 1 second.

14. The apparatus of claim 13 wherein the time is about 0.56 seconds.

15. The apparatus of claim 11 wherein the light source is a laser diode.

16. The apparatus of claim 11 further comprising a feedback control that is formed to determine a thermal relaxation time of the incision.

17. The apparatus of claim 11 wherein at least a portion of the housing is transparent.

18. A method for controlling a fluid collection incision, the method comprising:
    providing a sampling apparatus having a housing, a lancet with an end formed to create a fluid collection incision, and a light source,
    lancing a portion of skin of a user with the end of the lancet to create a fluid collection incision, and
    exposing the fluid collection incision to light from the light source having a pre-determined wavelength and for a time sufficient to seal the incision following withdrawal of blood.

19. The method of claim 18 further comprising the step of collecting a blood sample from the fluid collection incision before the incision is exposed to said light.

20. The method of claim 18 wherein the pre-determined wavelength ranges from about 400 nm to about 1400 nm.

21. The method of claim 18 wherein the fluid collection incision is exposed to the light for a time ranging from about 0.1 second to about 1 second.

\* \* \* \* \*